US005622779A

United States Patent [19]
Davis

[11] Patent Number: 5,622,779
[45] Date of Patent: Apr. 22, 1997

[54] CELLULAR FACTORS THAT REGULATE THE EXPRESSION OF GENES ENCODING PROTEINS INVOLVED IN CHOLESTEROL HOMEOSTASIS AND METHODS OF USING SAME

[75] Inventor: Roger Davis, Solana Beach, Calif.

[73] Assignee: San Diego State University Foundation, San Diego, Calif.

[21] Appl. No.: 250,810

[22] Filed: May 27, 1994

[51] Int. Cl.$^6$ ................................................ A61K 35/12
[52] U.S. Cl. ............................................................ 424/520
[58] Field of Search ............................................... 424/520

[56] References Cited

PUBLICATIONS

Everson, Gregory T., "Bile Acid Metabolism and Its Role in Human Cholesterol Balance." Sem. Liver Disease. 12:420–427 (1992).

Vlahcevic, Z.R., et al., "Function and Regulation of Hydroxylases Involved in the Bile Acid Biosynthesis Pathways." Sem. Liver Disease. 12:403–419 (1992).

Havel, Richard J., "Role of Liver in Hyperlipidemia." Sem. Liver Disease. 12:356–363 (1992).

Davis, Roger A. et al., "Bile Acid Synthesis and the Enterohepatic Circulation: Processes Regulating Total–Body Cholesterol Homeostasis." Molecular Genetics of Coronary Heart Disease and Stroke. (ed. Lusis et al., Karger Press). 208–227 (1992).

Davis, Roger A. et al., "Examination of Bile Acid Negative Feedback Regulation in Rats." J. Lipid Research. 29:202–211 (1988).

Davis, Roger A. et al., "Bile Acid Secretion by Cultured Rat Hepatocytes." J. Biol. Chem. 258:3661–3667 (1983).

Davis, Roger A. et al., "Bile Acid Synthesis by Cultured Hepatocytes." J. Biol. Chem. 258:4079–4082 (1983).

Taniguchi, Takahiro et al., "Regulation of Cholesterol 7 α–Hydroxylase Gene Expression in Hep–G2 Cells." J. Biol. Chem. 269:10071–10078 (1994).

*Primary Examiner*—John W. Rollins
*Attorney, Agent, or Firm*—Campbell & Flores

[57] ABSTRACT

The present invention provides a substantially purified cellular factor that can regulate the expression of genes that encode proteins involved in cholesterol metabolism. The invention also provides methods of obtaining the cellular factors of the invention in a substantially purified form. The invention further provides a method of using a cellular factor of the invention to reduce cholesterol levels in a subject having hypercholesterolemia comprising administering a cellular factor to the subject.

17 Claims, 4 Drawing Sheets

7 ALPHA HYDROXYLASE INDUCTION BY CHO-K1 FRACTIONS

CELLULAR FACTORS THAT REGULATE THE EXPRESSION OF GENES ENCODING PROTEINS INVOLVED IN CHOLESTEROL HOMEOSTASIS AND METHODS OF USING SAME

BACKGROUND OF THE INVENTION

1. Field of the Invention

This invention relates generally to the fields of gene regulation and molecular medicine and more specifically to the regulation of cholesterol metabolism.

2. Background Information

Heart disease is the number one killer of people in developed countries and, along with stroke, accounts for more than half of the deaths due to pathological causes. Heart attacks usually occur when coronary arteries become narrowed due to atherosclerosis, which is initiated by the accumulation of cholesterol deposits on or within the cells of the blood vessel wall to form atherosclerotic plaques. As a result of the cholesterol accumulation and smooth muscle cell proliferation, a narrowing of the internal diameter of the blood vessel occurs and can reach a stage where blood can no longer circulate past the narrowed vessel. The incidence of stroke increases with the formation of atherosclerotic plaques. The result of blood vessel blockage is that cells that form the tissues downstream of the blockage die due to lack of oxygen or nutrition or to build-up of toxic metabolic waste products. As a result, cardiac function or brain function can be impaired.

One of the most important risk factors associated with atherosclerotic heart disease is the concentration in the blood of low density lipoprotein (LDL), which, in humans, is the major carrier of cholesterol in the form of cholesterol esters. Normally, LDL is cleared from the blood by the liver. However, in a subject having impaired expression of the LDL receptor (LDL-R), LDL clearance may be inadequate and the LDL concentration in the blood can increase. In addition, some people are genetically predisposed to having high LDL levels due, for example, to alterations in one of the many genes involved in the metabolic pathway for cholesterol and lipoprotein metabolism. As a result of each of these conditions, blood LDL levels are elevated or high density lipoprotein (HDL) levels are decreased, atherosclerosis develops and, in severe cases, a heart attack or stroke occurs.

In a person having a moderately high level of cholesterol in the blood, termed hypercholesterolemia, intervention therapy often can reduce cholesterol to a near normal level. For example, simple changes in the diet and initiation of a program of exercise can sometimes control blood levels of LDL and HDL. As the level of hypercholesterolemia increases, medical intervention becomes necessary. Various drugs that block cholesterol synthesis or increase the expression of hepatic LDL-R may decrease the blood cholesterol level. However, the available drugs suffer various shortcomings including lack of specificity, a lack of potency and adverse side effects.

Drug treatment cannot adequately reduce cholesterol blood levels in cases of extreme hypercholesterolemia or in cases where a genetic defect results in the inability to express hepatic LDL-R. In these cases, a liver transplant may offer the only reasonable hope of effectively treating a patient. For example, transplantation of a normal liver into a prematurely atherosclerotic female decreased plasma LDL levels to normal and resulted in a regression of atherosclerotic lesions (Bilheimer et al, *New Engl. J. Med.* 311: 1658–1664 (1984). Of course, the risks associated with transplantation are well documented. Recently, gene therapy has been reported to reduce the levels of cholesterol in a person having a genetic defect that resulted in severe hypercholesterolemia. However, methods for performing gene therapy remain experimental and have not been proven to be effective over a prolonged period of time.

Thus, a need exists for potent, specific agents that can effectively reduce blood cholesterol levels and, thereby, reduce or prevent the occurrence of heart attacks and strokes. The present invention satisfies this need and provides additional advantages as well.

SUMMARY OF THE INVENTION

The present invention provides substantially purified cellular factors that can regulate the expression of genes encoding proteins involved in cholesterol homeostasis. For example, a cellular factor of the invention can induce the expression of a gene encoding 7α-hydroxylase or can repress the expression of a gene encoding β-hydroxy-β-methylglutaryl coenzyme A (HMG-CoA) reductase.

The invention also provides methods of obtaining substantially purified cellular factors that can regulate the expression of genes encoding proteins involved in cholesterol homeostasis. The invention further provides methods of using the cellular factors to reduce cholesterol levels in a subject having hypercholesterolemia by administering a cellular factor to the subject.

DETAILED DESCRIPTION OF THE INVENTION

Figure 1:
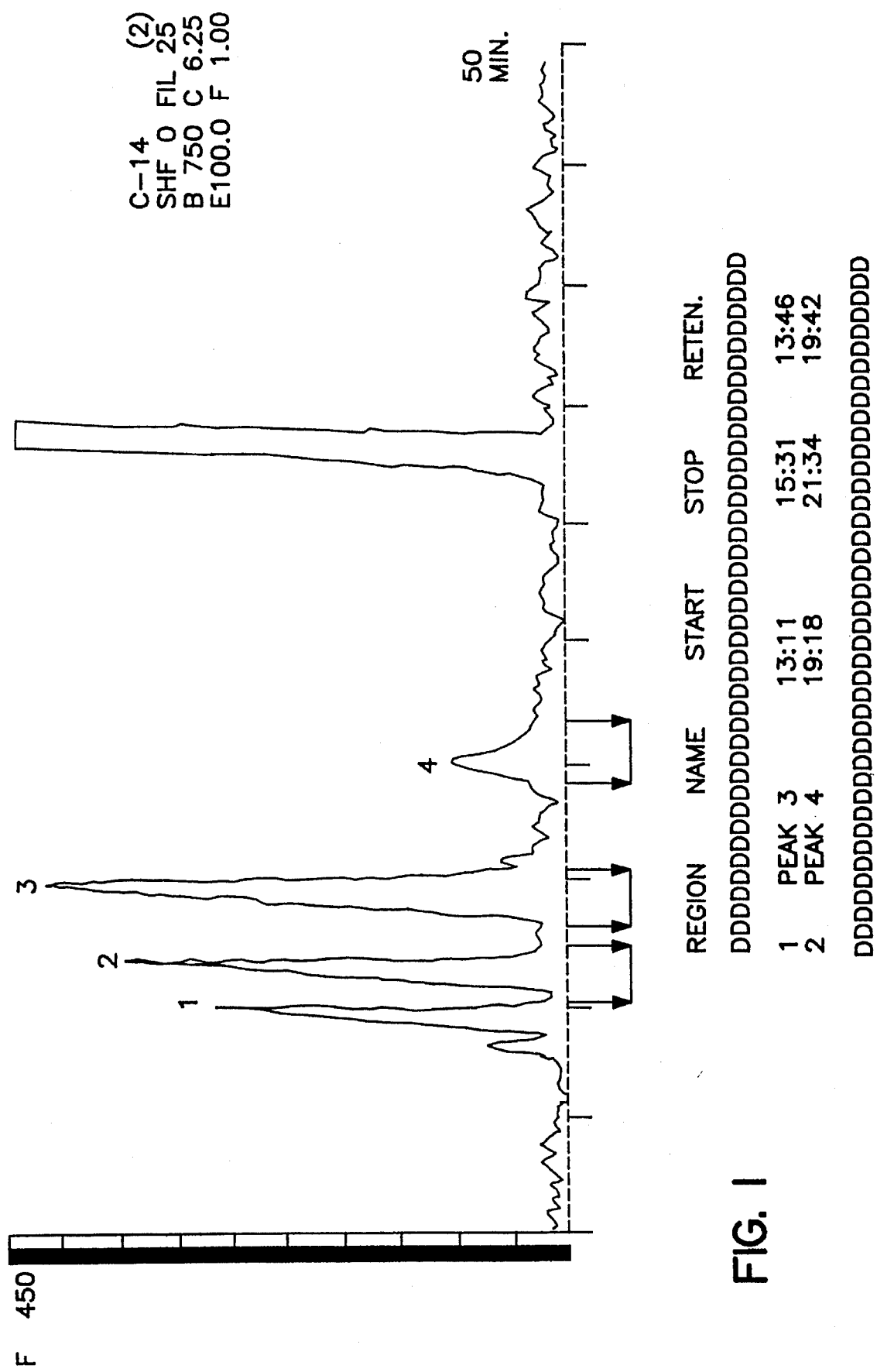
FIG. 1 shows the isolation of cellular factors of the invention by the reverse phase-high performance liquid chromatography (RP-HPLC) elution pattern of the hexane extract obtained from Chinese hamster ovary (CHO) K1 cells. Peaks 1 to 4 are labelled. X-axis is arbitrary units indicating the relative amount of radioactivity; Y-axis is time of elution. Bars indicate fractions pooled for peak 2, peak 3 and peak 4.

The present invention provides substantially purified cellular factors that can regulate the expression of various genes that encode proteins involved in cholesterol homeostasis. For example, the cellular factors of the invention can induce the expression of a gene encoding 7α-hydroxylase, which is an enzyme involved in the catabolism of cholesterol, or can repress the expression of a gene encoding β-hydroxy-β-methylglutaryl coenzyme A (HMG-CoA) reductase, which is involved in the synthesis of cholesterol. These and other proteins, including, for example, HMG-CoA synthase, farnesyl diphosphate synthetase and squalene synthase, that are involved in maintaining cholesterol homeostasis are known in the art (see, for example, Devlin, *Textbook of Biochemistry With Clinical Correlations* (Wiley-Liss 1992); see pages 438–449, which are incorporated herein by reference).

As used herein, the term "cholesterol homeostasis" refers to the steady-state level of cholesterol in a normal mammal, including a human. In general, a human who is at low risk for developing heart disease has a plasma cholesterol level of about 100–150 mg %. This plasma cholesterol level is maintained by various enzymes that mediate the uptake, synthesis and catabolism of cholesterol. Cholesterol homeostasis normally can be maintained within a range of 100–150 mg % if the expression of genes encoding proteins such as 7α-hydroxylase, HMG-CoA reductase and other proteins as described herein or otherwise known to those in the art can be maintained at a desirable level. The cellular factors of the invention can regulate the expression of such genes.

As used herein, the term "cellular factor" or "factor" means a biochemical substance that is produced in a cell or a modified form of such a substance. A cellular factor can be produced de novo in the cell or can be an intermediate or an end-product of a metabolic or catabolic process that occurs in a cell. For example, a cellular factor can be an oxysterol, which is a hydroxylated form of a cholesterol molecule that has been produced by a cytochrome P450-dependent hydroxylation reaction in the cell.

A cellular factor can be modified such that the factor has a desirable property, such as increased stability in vivo, provided that such modification does not result in the cellular factor losing its activity of regulating the expression of a gene encoding a protein involved in cholesterol homeostasis. In general, a modification of a cellular factor can be a chemical modification such that a particularly labile or reactive site is made less labile or less reactive, thereby stabilizing the cellular factor. In addition, it can be desirable to modify a cellular factor for various other purposes, including, for example, to modify the activity of the factor or the ability of the factor to be absorbed through the skin or via the alimentary tract, or to make the factor less stable, so that it effects its functional activity for a shorter period of time. Since such modified cellular factors maintain the ability to regulate the expression of a gene encoding a protein involved in cholesterol homeostasis, such modified cellular factors are included within the meaning of the term "cellular factor" as used herein.

A cellular factor of the invention also can be modified so as to contain a detectable label. Detectable labels are known in the art and include, for example, radionuclides and fluorochromes. Such detectable labels can be attached to a cellular factor or can be incorporated into the structure of the cellular factor. For example, non-radioactive isotopes can be incorporated into a cellular factor of the invention to facilitate determining the chemical structure of the factor. A detectable label can be chemically attached to a cellular factor of the invention or can be incorporated into the factor metabolically by incubating a cell producing the factor in the presence of an appropriate precursor (see Example I).

The term "substantially purified" is used herein to mean that a cellular factor of the invention is in a form that is relatively free of other biological molecules such as lipids, proteins or nucleic acids with which the cellular factor normally is associated in a cell in nature. A cellular factor that is produced using methods of chemical synthesis is an example of a substantially purified cellular factor as is a cellular factor that is obtained using, for example, the biochemical methods disclosed in Example I. Thus, an enriched fraction obtained by RP-HPLC under the conditions set forth in Example I, such as the fractions designated peak 2, peak 3 and peak 4, are examples of substantially purified cellular factors of the invention.

A substantially purified cellular factor of the invention is characterized, in part, by its functional activity of regulating the transcriptional activity of a gene encoding a protein that is involved in cholesterol homeostasis. It is known that transcriptional regulation of the LDL-R gene (Taylor et al., *J. Biol. Chem.* 259: 12382–12387 (1984); Dawson et al., *J. Biol. Chem.* 263: 3372–3379 (1988), each of which is incorporated herein by reference) and the HMG-CoA reductase gene (Osborne et al., *J. Biol. Chem.* 267: 18973–18982 (1992), which is incorporated herein by reference), for example, is an important factor controlling the activity of each enzyme in vivo. Oxysterols, which are hydroxylated forms of cholesterol, likely are involved in the transcriptional regulation of the LDL-R gene (Taylor et al., supra, 1984; Goldstein and Brown, *Nature* 343: 425–430 (1990)). However, prior to the present invention, the specific cellular factor(s) that regulate the genes encoding proteins involved in cholesterol homeostasis, including, for example, the 7α-hydroxylase gene, were not identified or obtained in substantially purified form.

As used herein, the term "regulate" means that the cellular factor can effect the transcriptional activity of a gene that encodes a protein involved in cholesterol homeostasis. For example, a cellular factor of the invention can up-regulate the expression of a gene such as the 7α-hydroxylase gene. As used herein, the term "up-regulate" means that the transcriptional activity of a gene is increased to a greater level than occurs in the absence of a cellular factor. Up-regulation of a gene can occur, for example, due to induction or to derepression of a gene that is transcriptionally inactive or is expressed at a relatively low level. Thus, the term "up-regulate" is synonymous with the terms "induce" or "derepress" as used herein.

A cellular factor of the invention also can down-regulate the expression of a gene such as the HMG-CoA reductase gene. As used herein, the term "down-regulate" means that the transcriptional activity of a gene is decreased to a lower level than occurs in the absence of a cellular factor. Down-regulation of a gene can occur, for example, due to the repression of a transcriptionally active gene. Thus, the term "down-regulate" is synonymous with the term "repress" as used herein. Use of the terms "up-regulate" or "down-regulate" is not intended to indicate that the cellular factors of the invention effect their function through a particular mechanism of action. Methods for identifying the gene regulatory activity of the cellular factor of the invention are described in detail, below, or otherwise known in the art.

A cellular factor of the invention can regulate gene expression directly or by binding to a cellular protein, which, in turn, can act as a transcription factor to regulate gene expression. A cellular factor of the invention also can indirectly regulate expression of a second gene due the action of the cellular factor on a first gene. For example, in the liver, a cellular factor of the invention can induce the expression of the 7α-hydroxylase gene and can repress expression of the HMG-CoA reductase gene. However, upon expression, 7α-hydroxylase can metabolize the inducing cellular factor, which can be a substrate for 7α-hydroxylase (see, for example, Swell et al., Biochim. Biophys. Acta 663: 163–168 (1981); Ayaki et al., J. Biol. Chem. 264: 3818–3821 (1989)). As a result of the decreased level of a cellular factor in the cell due to 7α-hydroxylase activity, derepression of the LDL-R gene, for example, can occur (see, for example, Dueland, et al., J. Biol. Chem. 267: 22695–22698 (1992), which is incorporated herein by reference).

A substantially purified cellular factor of the invention also can be characterized by various physical, chemical and biological properties. For example, a cellular factor of the invention can be excreted from non-hepatic cells such as Chinese hamster ovary (CHO) cells, which do not express 7α-hydroxylase. As used herein, the term "excreted" is used in its broadest sense to mean that the cellular factors can be found exterior to the cell such as in the medium of the cells in culture ("conditioned medium"). Use of the term "excreted" does not imply that a cellular factor of the invention is passed from the cell as a metabolic waste product or by any particular mechanism. For example, a cellular factor of the invention can be actively or passively transported from a cell or may simply diffuse from a cell. Thus, the mechanism by which a cellular factor of the invention appears external to the cell is irrelevant with regard to the use herein of the term "excreted." Since the cellular factors of the invention are excreted, they can be substantially purified, for example, from the conditioned medium of non-hepatic cells such as CHO cells as described in Example I. A cellular factor of the invention also can be characterized, in part, by its elution profile using reverse phase-high performance liquid chromatography (RP-HPLC) under the conditions described in Example I.

The liver is the primary organ for removing cholesterol from the blood plasma and eliminating it from the body. The liver has three unique characteristics that contribute to this function. First, liver parenchymal cells are surrounded by a porous, fenestrated endothelial surface, which allows optimal interaction of plasma components such as LDL with surface membrane proteins such as the LDL-R. Second, unlike non-liver cells, in which LDL-R expression is almost completely repressed in response to the level of cellular cholesterol, the LDL-R is only partially down-regulated in liver cells (Pangburn et al., J. Biol. Chem. 256: 3340–3347 (1981); Edge et al., J. Biol. Chem. 261: 3800–3806 (1986)). Third, the liver is the only organ that contains cells expressing 7α-hydroxylase (Jelinek et al., J. Biol. Chem. 265: 8190–8197 (1990), which is incorporated herein by reference; Lavery and Schibler, Genes Devel. 7: 1871–1884 (1993)), which is the enzyme involved in the first and rate-limiting step in bile acid synthesis. As described below, cells in culture that do not express 7α-hydroxylase are killed by synthetic oxysterols such as 25-hydroxycholesterol.

Cellular cholesterol concentrations regulate the expression of genes that are responsible for the uptake (LDL-R), synthesis (HMG-CoA synthase, HMG-CoA reductase, farnesyl-diphosphate synthase, squalene synthetase) and catabolism (7α-hydroxylase) of cholesterol. In non-hepatic cells, an elevated level of cellular cholesterol represses the expression of genes encoding proteins involved in cholesterol uptake and synthesis. In liver cells, elevated cholesterol levels repress the expression of genes involved in cholesterol synthesis and induce the expression of genes encoding proteins involved in cholesterol catabolism. Thus, cholesterol homeostasis in the body is maintained by multiple levels of control.

While cellular cholesterol levels are related to the level of expression of the proteins involved in cholesterol homeostasis, cholesterol, itself, does not regulate the expression of the genes encoding these proteins. Instead, one or more metabolites of cholesterol such as oxysterols, which are hydroxylated forms of cholesterol, likely regulate the expression of these genes. A role for cholesterol metabolites as the cellular factors that regulate genes involved in cholesterol homeostasis is supported by experiments in which non-hepatic cells were treated with ketoconazole, which inhibits cytochrome P450-dependent hydroxylation reactions, including hydroxylation of cholesterol to form oxysterols. In the absence of ketoconazole, the addition of LDL to the cells decreased expression of the LDL-R. In contrast, in ketoconazole-treated cells, LDL no longer down-regulated the expression of the LDL-R (Takagi et al., J. Biol. Chem. 264: 12352–12357 (1989)). However, addition of a synthetic oxysterol, 25-hydroxycholesterol, to the ketoconazole-treated cells resulted in almost complete suppression of LDL-R expression. These results indicate that, in the presence of cholesterol, non-hepatic cells, which do not express 7α-hydroxylase, produce a repressor that functions like 25-hydroxycholesterol and represses expression of the LDL-R gene. Down-regulation of the LDL-R in non-hepatic cells decreases the uptake of cholesterol by the cells.

Expression of 7α-hydroxylase, which normally is expressed only in liver cells, effects the conversion of cholesterol to bile acids, thus facilitating clearance of cholesterol from the body. Expression of 7α-hydroxylase is regulated, in part, by the enterohepatic circulation of bile acids (Myant and Mitropoulis, J. Lipid Res. 18: 135–153 (1977)). For example, diversion of bile acids from the enterohepatic circulation by bile duct cannulation of rats (Davis et al., J. Lipid Res. 29: 202–211 (1988)) or by feeding rats cholestyramine, which binds to bile acids and facilitates their excretion (Myant and Mitropoulis, supra, 1977) resulted in a 3–5× increase in 7α-hydroxylase activity. Conversely, feeding bile acids to rats decreased 7α-hydroxylase activity (Straka et al., J. Biol. Chem. 265: 7145–7149 (1990)). The inhibition of 7α-hydroxylase activity in response to increased bile acids is associated with a decreased relative abundance of 7α-hydroxylase mRNA, which likely is due to decreased transcription of the 7α-hydroxylase gene (see Waxman, J. Ster. Biochem. Mol. Biol. 43: 1055–1072 (1992)).

Cellular cholesterol levels also have a role in regulating expression of 7α-hydroxylase in liver cells. However, in contrast to its effect of down-regulating the expression a gene such as the HMG-CoA reductase gene, cholesterol up-regulates 7α-hydroxylase gene expression (Jelinek et al, supra, 1990; Pandak et al., J. Biol. Chem. 266: 3416–3421 (1991); Leighton et al., supra, 1991). For example, feeding cholesterol to rats transcriptionally activates 7α-hydroxylase gene expression in the liver (Pandek et al., supra, 1990). In addition, by providing increased cholesterol, which ultimately is a substrate for 7α-hydroxylase, increased formation of bile acids occurs (Straka et al., *J. Biol. Chem.* 265: 7145–7149 (1990)). The increased bile acids, in turn, can down-regulate 7α-hydroxylase expression by a feedback mechanism.

The promotor elements and transcription factors for the HMG-CoA reductase gene (Osborne et al., supra, 1992) and the LDL-R gene (Briggs et al., *J. Biol., Chem.* 268: 14490–14496 (1993); Wang et al., *J. Biol. Chem.* 268: 14497–14504 (1993); Yokoyama et al., *Cell* 75: 187–197 (1993)) have been described. Each promotor contains a sterol regulatory element (SRE) consisting of CG-rich decanucleotides that differ by a single base. The promotors are conditional positive promotors, which up-regulate transcription in the absence of the DNA binding proteins, however, the transcription factors are specific for each SRE. Thus, repression of the HMG-CoA reductase and the LDL-R by a cellular factor can be regulated independently.

The promotor elements of the 7α-hydroxylase gene do not contain cross-species conserved sequences to the SRE (Jelinek and Russell, *Biochemistry* 29: 7781–7785 (1990); Crestani et al., *Arch. Biochem. Biophys.* 306: 451–460 (1993); Molowa et al., *Biochemistry* 31: 12539–2544 (1992)) and, therefore, are distinct from those of the HMG-CoA reductase gene and the LDL-R gene. In particular, the SRE for the 7α-hydroxylase promotor may be condition negative, which down-regulates transcription in the absence of the DNA binding proteins. As disclosed herein, the cellular factors of the invention possess the divergent ability to down-regulate transcription of genes such as HMG-CoA reductase, the LDL-R and squalene synthetase, which are down-regulated in non-hepatic cells by elevated levels of cholesterol, and up-regulate the activity of a gene such as 7α-hydroxylase, which is up-regulated in liver cells by elevated levels of cholesterol.

The present invention also provides a method for obtaining the cellular factors of the invention in a substantially purified form. As disclosed herein, the unexpected finding that the cellular factors are excreted from cells that do not express 7α-hydroxylase provided a means for obtaining the factors from conditioned medium. As used herein, the term "conditioned medium" means the cell culture medium in which cells such as wild-type CHO-K1 cells have been grown (see Example I).

In order to identify the presence of the cellular factors of the invention during purification, an appropriate in vitro assay system was required. The L35 rat hepatoma cell line provided a useful model system for identifying cellular factors that regulate the expression in liver cells of genes involved in cholesterol homeostasis such as the 7α-hydroxylase gene. L35 cells were obtained by transfecting H35 rat hepatoma cells, which do not express 7α-hydroxylase, with human HepG2 cell genomic DNA and selecting for resistance to 25-hydroxycholesterol (Leighton et al., *Mol. Cell. Biol.* 11: 2049–2056 (1991), which is incorporated herein by reference). L35 cells express the rat 7α-hydroxylase gene.

Cells such as non-hepatic cells and various cultured hepatocyte-derived cells such as H35 cells do not express 7α-hydroxylase and, therefore, are killed by the synthetic oxysterol, 25-hydroxycholesterol, which kills cells by repressing the expression of genes encoding proteins responsible for cholesterol uptake and synthesis. L35 cells are resistant to killing by 25-hydroxycholesterol because 7α-hydroxylase can metabolize 25-hydroxycholesterol and inactivate its repressor activity.

Figure 4:
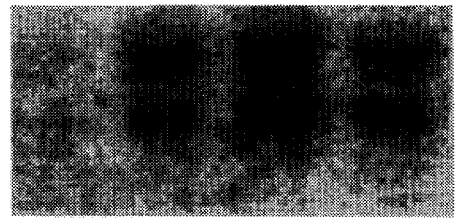
FIG. 4 shows the levels of 7α-hydroxylase mRNA induced in L35 cells by the cellular factors of the invention. Cells were incubated for 24 hr in serum-free medium containing 1 µg/ml 25-hydroxycholesterol and 10 µg/ml cholesterol ("C") or cellular factors of peak 2 ("1"), peak 3 ("2") or peak 4 ("3").

The regulation of 7α-hydroxylase gene expression in L35 cells has been well characterized and correlates with the regulation of this gene in rat liver (see, for example, Leighton et al., supra, 1991). For example, when L35 cells are cultured in serum-free medium, 7α-hydroxylase mRNA and 7α-hydroxylase activity are undetectable. However, addition of dexamethasone, which induces 7α-hydroxylase in rat hepatocytes (Princen et al., *Biochem. J.* 262: 341–348 (1989), to the serum-free medium resulted in a rapid induction of 7α-hydroxylase mRNA and activity (Leighton et al., supra, 1991). As disclosed herein, the cellular factors of the invention also can induce expression of the 7α-hydroxylase gene as indicated by increased 7α-hydroxylase mRNA levels in L35 cells incubated with the factors (see Example II and FIG. 4).

L35 cells also express mRNA encoding various liver-specific proteins such as glucokinase (Iynedjian, et al., *J. Biol. Chem.* 262: 6032–6038 (1987)), the sodium dependent bile acid transporter (Hagenbuch et al., *Proc. Natl. Acad. Sci., USA* 88: 10629–10633 (1991)), ecto-ATPase (Lin et al., *J. Biol. Chem.* 264: 14408–14414 (1989)) and the microsomal cytochrome P450 (P4502E1; Dai et al, *Biochemistry* 32: 6928–6937 (1993)) at levels equal to or greater than the levels expressed in vivo. In addition, L35 cells form cell-cell contacts similar to the canaliculi of liver cells in vivo. L35 cells also display a hormone sensitive production of $^{14}C$-glucose from $^{14}C$-lactate. Thus, L35 cells exhibit an adult liver phenotype and, therefore, are an ideal model system for screening for cellular factors that regulate expression in the liver of the genes involved in cholesterol homeostasis.

The cellular factors of the invention were substantially purified from conditioned medium of wild-type CHO-K1 cells (K1 cells; see Example I). These cellular factors were shown to exist based on the following experiments. In order to examine the effect of 7α-hydroxylase gene expression in a cell, non-hepatic CHO-K1 cells were transfected with a nucleic acid sequence encoding 7α-hydroxylase (Dueland et al., supra, 1992). The transfected CHO cells, JD15 cells, expressed 7α-hydroxylase mRNA and exhibited 7α-hydroxylase activity. When cultured in the presence of 5% serum, expression of the LDL-R by JD15 cells was greater than 20× higher than expression in the parental K1 cells, even though the K1 cells had a 50% higher level of cholesterol ester (Dueland et al., supra, 1992).

The effect of 25-hydroxycholesterol on K1 and JD15 cells also was examined. Expression of the LDL-R was almost completely repressed by this synthetic oxysterol in both cell lines. This result indicates that transcriptional control of the LDL-R gene is intact in the transfected cells. However, derepression of the LDL-R gene occurred with time in the JD15 cells, which express 7α-hydroxylase. This transient sensitivity to 25-hydroxycholesterol repression likely is due to the 3× greater rate of metabolism of 25-hydroxycholesterol in the JD15 cells (Dueland et al., supra, 1992).

The paradoxical induction of LDL-R mRNA in the transfected JD15 cells, which accumulate greater amounts of cholesterol esters than K1 cells, indicates that natural oxysterols likely are a substrate for 7α-hydroxylase. In this regard, 7α-hydroxylase has been shown to selectively use the synthetic oxysterol, 27-hydroxycholesterol, but not cholesterol, as a substrate (Axelson et al., *J. Biol. Chem.* 267: 1701–1704 (1992). In JD15 cells, 7α-hydroxylase can indirectly induce LDL-R gene expression by metabolizing and inactivating an oxysterol repressor. A similar mechanism of action may prevent down-regulation of the LDL-R gene in liver cells.

Figure 2:
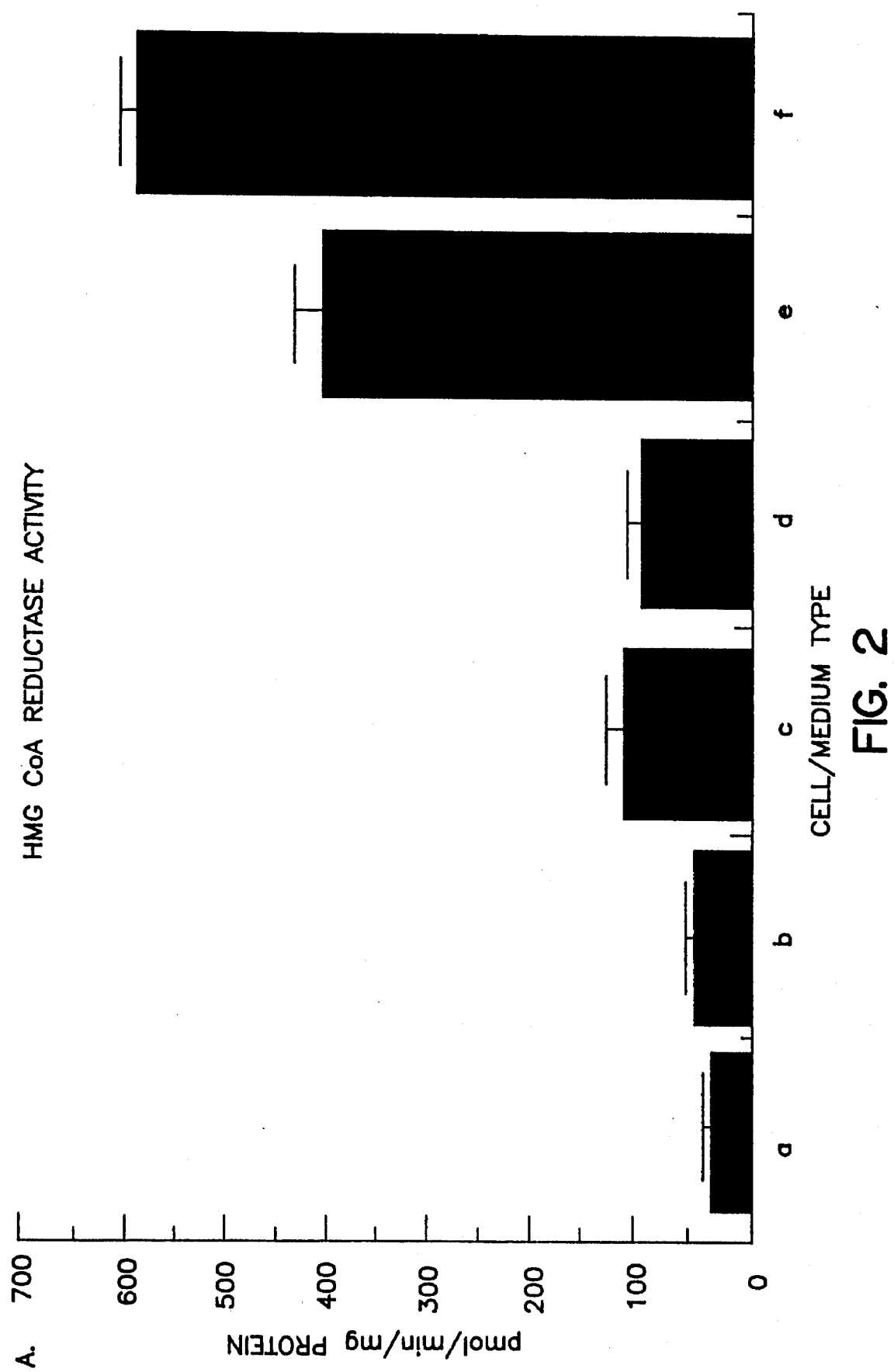
FIG. 2 demonstrates the activity of HMG-CoA reductase in wild-type CHO-K1 cells (lanes a–c) and in transfected CHO-JD15 cells, which express 7α-hydroxylase (lanes d–f). Cells were incubated in medium containing either 5% delipidated serum plus 50 µg/ml LDL (lanes a and d), 5% normal serum (lanes b and e) or 5% delipidated serum, alone (lanes c and f).

The activity of HMG-CoA reductase and squalene synthetase also was examined in JD15 cells as compared to K1 cells. Under all conditions examined, the activities of both HMG-CoA reductase (FIG. 2) and squalene synthetase (not shown) were as much as 10× higher in the JD15 cells, which express 7α-hydroxylase, as compared to the wild-type K1 cells. The increased activity correlated to increased levels of the respective mRNA's (not shown). Moreover, while the expression of both genes was induced in both cell lines when incubated in medium containing delipidated serum and was repressed in response to LDL, the activities were significantly higher in the JD15 cells (FIG. 2). Thus, expression of 7α-hydroxylase does not interfere with the ability of cholesterol to repress HMG-CoA reductase and squalene synthetase, although the level of transcription in these cells is higher than in CHO-K1 cells.

Since oxysterols, for example, exert their effect by regulating the transcriptional activity of genes encoding proteins involved in cholesterol homeostasis, CHO-K1 cells and JD15 cells were used to determine the effect of 7α-hydroxylase on the rate of transcription of HMG-CoA reductase. In order to minimize the likelihood that a mechanism other than transcriptional regulation of HMG-CoA reductase affected the result, a reporter gene was constructed consisting of the functional portion of the HMG-CoA reductase gene promotor linked to a nucleic acid sequence encoding the reporter molecule, luciferase (HMG-luc; Osborne et al., supra, 1992). The HMG-luc plasmid was transfected into JD15 cells and K1 cells. Luciferase activity was about 13.5-fold greater in JD15 cells as compared to K1 cells. Thus, the presence of 7α-hydroxylase activity in JD15 cells clearly increases the transcriptional activity of the HMG-CoA reductase promoter. These results indicate that 7α-hydroxylase activity either inactivates a cellular factor that represses transcription from the HMG-CoA reductase promotor or produces a cellular factor that derepresses transcription from the promotor.

In summary, HMG-CoA reductase, the LDL-R and squalene synthetase were markedly derepressed in JD15 cells, which express 7α-hydroxylase, as compared to wild-type K1 cells. In addition, JD15 cells had a markedly increased ability to metabolize the synthetic oxysterols, 25-hydroxycholesterol and 27-hydroxycholesterol. These results suggested that the levels of endogenous cellular factors such as oxysterols, which can regulate the expression of genes encoding proteins involved in homeostasis, may be significantly higher in cells such as CHO-K1 cells, which do not express 7α-hydroxylase, as compared to cells that express 7α-hydroxylase.

An attempt was made to isolate the cellular factors that regulate the expression of genes encoding protein involved in cholesterol homeostasis from wild-type CHO-K1 cell extracts. CHO-K1 cells and JD15 cells were incubated in the presence of $^{14}$C-acetate, which can label endogenous oxysterols, and cell extracts were prepared. The extracts were fractionated by RP-HPLC and silica gel HPLC and the eluted fractions were screened for labelled oxysterols using a radiation scintillation flow detector. However, the elution pattern was too complicated to discern a difference between labelled substances produced in the K1 cells as compared to JD15 cells.

When the same experiments were performed using conditioned medium from K1 or JD15 cells, instead of cell extracts, the conditioned medium from K1 cells showed a dramatic accumulation of labeled polar sterols in these RP-HPLC fractions (see FIG. 1, peaks 2, 3 and 4). The cellular factors present in these peaks inhibited the activity of endogenous HMG-CoA reductase activity in CHO-K1 cells by greater than 90%. In addition, the cellular factors in peak 2 (not shown) and in peaks 3 and 4 (FIG. 3) repressed the expression of the HMG-luc reporter construct, indicating that the effect occurs at the level of transcription. No toxic effect of the cellular factors of peaks 3 and 4 was observed and there was no significant effect on cell protein. A factor in peak 2, however, was toxic to CHO-K1 cells but not to L35 cells.

The reduction in luciferase activity was similar to the reduction that occurred when 25-hydroxycholesterol (1 μg/ml) and cholesterol (10 μg/ml) in ethanol were added together to the cells. Assuming that the UV absorption at 210 nm of these cellular factors is due to oxysterols and that the UV absorption by these factors is equivalent to the absorption of 25-hydroxycholesterol, the cellular factors of the invention are approximately 500× more potent than 25-hydroxycholesterol in repressing transcription of the HMG-CoA reductase gene. Since the medium that was not incubated with K1 cells did not contain repressor activity, the activity of peaks 2, 3 and 4 was not due to a contaminant present in the medium. Furthermore, the cellular factors present in these peaks did not correspond to other putative oxysterols such as 25-hydroxycholesterol, 27-hydroxycholesterol, 32-oxylanosterol or 24(S), 25-epoxycholesterol.

Analysis of peak 3 and peak 4 by silica gel-HPLC and GC/mass spectroscopy indicated that different cellular factors were present in these fractions. Thus, peaks 3 and 4 contain at least two distinct cellular factors that can regulate the expression of genes encoding proteins involved in cholesterol homeostasis.

The cellular factors of the invention can induce the expression of the 7α-hydroxylase gene in L35 cells, which are phenotypically similar to adult liver hepatocytes. Incubation of L35 cells with the cellular factors present in peaks 2, 3 and 4 results in increased levels of 7α-hydroxylase mRNA (FIG. 4), indicating that the cellular factors of the invention act at the transcriptional level in up-regulating expression of the 7α-hydroxylase gene.

The substantially purified cellular factors of the invention can be further purified using the methods described below (see Example I) or otherwise known in the art. Thus, each factor can be obtained in isolated form. Similarly, the cellular factors can be further characterized by determining, for example, the molecular size, chemical structure or other functional or structural characteristics of the factors.

The present invention also provides methods of using a cellular factor of the invention to reduce the level of plasma cholesterol in a subject having hypercholesterolemia. A plasma cholesterol level less than about 150 mg % is desirable in humans. Similarly, a desirable plasma cholesterol level can be determined for mammals other than humans. As plasma cholesterol levels increase to between above about 150 mg % in humans, the risk of atherosclerosis begins to increase proportionately. Thus, it is desirable to reduce the level of plasma cholesterol in a subject having hypercholesterolemia. As used herein, the term "hypercholesterolemia" means a plasma cholesterol level that is above about 150 mg % in a human or is above a desirable plasma cholesterol level in a mammal other than a human. In general, a subject having hypercholesterolemia has an increased likelihood of suffering a heart attack or stroke. The present invention provides a method of treating a subject having hypercholesterolemia by administering a cellular factor of the invention to the subject in order to reduce the plasma cholesterol level in the subject.

As used herein, the term "reduce" means that the cellular factor can decrease the plasma cholesterol level in a subject as compared to the level in the subject prior to receiving the factor. Since the cellular factors can reduce the plasma cholesterol levels in a subject having hypercholesterolemia, the cellular factors of the invention are useful in the preparation of medicaments. Currently, drugs such as cholestyramine, which induces 7α-hydroxylase, or lovastatin, which represses expression, for example of the LDL-R and HMG-CoA reductase, are used to regulate plasma cholesterol levels in a subject having hypercholesterolemia. However, use of a cellular factor of the invention to reduce plasma cholesterol levels in a subject provides an advantage over drug therapy in that the subject is treated with a naturally occurring biological substance or a modified form thereof, which can minimize the likelihood of undesirable side effects. Furthermore, unlike other HMG-CoA reductase inhibitors, the cellular factors disclosed herein increase the level of mRNA encoding 7α-hydroxylase, thus providing a unique method to rid the body of excess cholesterol by increasing its conversion to bile acids.

If desired, a cellular factor of the invention can be administered as a pharmaceutical composition comprising a cellular factor and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters. A pharmaceutically acceptable carrier can contain physiologically acceptable compounds that act, for example, to stabilize the cellular factor of the invention or increase the absorption of the factor. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition and on the particular physicochemical characteristics of the specific cellular factor.

A cellular factor of the invention or a pharmaceutical composition containing a cellular factor of the invention can be administered to a subject by various routes including, for example, orally, by intubation or parenterally such as intravenously, intramuscularly or subcutaneously or by passive or facilitated absorption through the skin using, for example, a skin patch or transdermal iontophoresis, respectively. The effectiveness of a treatment using a cellular factor of the invention can be monitored using routine methods for determining, for example, plasma cholesterol levels or LDL levels in the subject at various times following administration of the factor. In addition, such monitoring is useful for determining whether an administered dose is adequate for producing the desired effect or whether the dose that is being administered should be adjusted. In general, the dose of a cellular factor can be decreased during the course of treatment, as the plasma cholesterol level in the subject decreases.

The following examples are intended to illustrate but not limit the present invention.

EXAMPLE I

Preparation of Substantially Purified Cellular Factors

This example describes methods for obtaining substantially purified cellular factors that regulate the expression of genes encoding proteins involved in cholesterol homeostasis.

The cellular factors were purified from conditioned medium of CHO-K1 cells. Cells were grown in 100 mm tissue culture plates containing 10 ml Dulbecco's minimal essential medium supplemented with 3.5% newborn calf serum and 1.5% fetal calf serum and containing 1× penicillin/streptomycin (standard medium). After the cells were confluent, the conditioned medium was removed and cellular factors were purified as described below.

In some experiments, the cells were incubated in the presence of $^{14}C$-acetate to label the cellular factors for use as tracers during purification. To radiolabel the cellular factors, the medium was removed when the cells were about 50–80% confluent and replaced with 5 ml of the same medium containing 20 μCi $^{14}C$-acetate (2.10 mCi/mol; 1 mCi/ml; Dupont-NEN; Boston, Mass.) and incubation was continued for 1–2 days.

The labelled and unlabelled conditioned media were extracted separately with an equal volume of hexane:isopropanol (3:2) (hexane extracts). For large volumes (100 ml) of hexane-extracted, unlabelled conditioned medium, the hexane extracts were concentrated to a final volume of about 5 ml by rotary evaporation. The hexane extracts were washed with an equal volume of phosphate buffered saline (PBS; pH 7.4), then dried under nitrogen.

Dried hexane extracts were resuspended in about 1 ml methanol:water (90:10) and approximately 2000 cpm of the resuspended labelled extract was added to the resuspended unlabelled extract (methanol:water sample). The methanol:water sample was loaded on a C18 SepPak column (Waters Associates; Milford, Mass.), which had been pre-conditioned with the methanol:water solvent. The samples were allowed to flow through the column by gravity, then were eluted using 5 ml of the methanol:water solvent. Cholesterol and other lipids either were insoluble in the solution or remained bound to the column. Negligible radioactivity eluted with the methanol:water solvent after 5 ml of elution. The methanol:water eluate ("polar fraction") was dried under nitrogen and stored under nitrogen. All reagents for extraction and chromatography were HPLC grade and obtained from Fisher Scientific (Pittsburgh, Pa.) or EM Separations (Gibbstown, N.J.).

The polar fraction was resuspended in 1 ml 100% ethanol and was fractionated by RP-HPLC using an Altex Ultrasphere ODS column (10 mm×25 cm; Altex-Beckman; Fullerton, Calif.). Elution was with acetonitrile:methanol (70:30) using a flow rate of 2.5 ml/min. Cholesterol and esters were not eluted within 60 min using this method, but could be eluted with ethanol. Radiolabelled cellular factors were identified using a radiation scintillation flow detector. The HPLC system consisted of Beckman 110A pumps, a Beckman 420 controller, Beckman LC332 gradient mixer, a Perkin-Elmer diode array detector model 235 (The Perkin-Elmer Corp.; Norwalk, Conn.), to detect UV absorption, and an INUS B-RAM radioactivity detector with either a solid yttrium detector (used for fraction collection) or a liquid scintillation counting (LSC) detector (INUS; Florida). For LSC detection, Ecolite(+) (ICN Biomedicals; Irvine Calif.) was pumped at a ratio of 2:1 column eluate. Total radioactivity of samples to be analyzed by HPLC was measured by LSC in a Beckman 1901 counter.

Using the conditions described above, the radiolabelled cellular factors eluted within 30 min (FIG. 1). Standards consisting of 25-hydroxycholesterol (Sigma; St. Louis Mo.) and 7α-hydroxycholesterol (Steraloids; Eilton, N.H.) eluted at 16 min and 20 min, respectively.

At least four peaks of radiolabelled cellular factors were obtained (FIG. 1). As described in Example II, below, peak 2 (11.27 min), peak 3 (13.46 min) and peak 4 (19.42 min) each contained one or more cellular factors that repressed expression of the HMG-CoA reductase gene in CHO-K1 cells and that induced expression of the 7α-hydroxylase gene in L35 cells.

If desired, peaks 2, 3 and 4 each can be further fractionated until the cellular factor(s) in each peak is obtained in an isolated form. For example, peaks 2, 3 and 4 can be further purified by HPLC using a silica gel support or any of various other supports available. In addition, the cellular factors can be further purified by varying the elution conditions. After each HPLC fractionation, individual peaks having repressor and/or inducer activity can be identified using the assays described in Example II.

As the number of irrelevant substances are removed from a peak containing a cellular factor of the invention, the chemical structure of a cellular factor can be determined using gas chromatography/mass spectroscopy. If GC/MS shows that there is more than one compound present in an HPLC peak, the structure of each factor can be determined, if possible, or another purification step can be performed. If GC/MS cannot yield an unambiguous structure, other methods such nuclear magnetic resonance spectroscopy can be employed. Using these methods, the individual cellular factors of the invention can be isolated and the chemical structures can be determined.

EXAMPLE II

Characterization of Cellular Factor Activity

This example describes the assays used to identify the presence of a cellular factor in a sample and to characterize the ability of a cellular factor to up-regulate or down-regulate a gene encoding a protein involved in cholesterol homeostasis.

A. Down-regulation of HMG-CoA Reductase Gene Expression

HMG-CoA reductase activity was assayed in wild-type CHO-K1 cells, which are a well recognized model system for investigating regulation of genes encoding proteins involved in cholesterol homeostasis (see, for example, Krieger et al., *J. Mol. Biol.* 150: 167–184 (1981); Cadigan et al., *J. Cell Biol.* 110: 295–308 (1990)). Cells were isolated at various times after addition of the polar fraction. HMG-CoA reductase activity was determined using the method of Shapiro et al. (*Biochim. Biophys. Acta* 370: 369–374 (1974), which is incorporated herein by reference) as modified by Rusnak and Krisans (*Biochem. Biophys. Res. Comm.* 148: 890–895 (1987), which is incorporated herein by reference). Protein was determined by a modification of the Lowry method (Hartree, *Anal. Biochem.* 48: 422–427 (1972), which is incorporated herein by reference). A dose-dependent decrease in HMG-CoA reductase activity was evident following 18–24 hr incubation in the presence of the extract (not shown).

In order to more efficiently identify the presence of a cellular factor that can repress the expression of HMG-CoA reductase, an assay was developed to directly determine whether an HPLC fraction contains an activity that can repress expression from the HMG-CoA reductase gene promotor. CHO-K1 cells were transfected with a plasmid construct containing the HMG-CoA reductase gene promotor (Osborne et al., supra, 1991) inserted into a plasmid containing a nucleic acid sequence encoding the luciferase reporter (Invitrogen; San Diego). The plasmid also contained a gene encoding that confers G418 (geneticin) resistance on a cell containing the plasmid.

K1 cells were transfected using the calcium phosphate method (Ausubel et al., *Current Protocols in Molecular Biology*, Suppl. 14: §§9.1.1–9.1.2 (John Wiley and Sons 1990), which is incorporated herein by reference) and were selected for G418 resistance. One colony of surviving cells (DH1 cells) was selected and expanded for use in these assays. DH1 cells were assayed for luciferase activity using the method of Brasier et al. (*Biotechniques* 11: 1116–1122 (1989), which is incorporated herein by reference), except that the lysis buffer was adjusted to contain 0.25% Triton-X100. Luciferin and standard luciferase were purchased from Sigma.

Briefly, DH1 cells were grown in 60 mm plates in standard medium for 2 days, at which time the cells were about 40% confluent ("Time 0"). Triplicate plates were assayed for each group. The standard medium was removed and 4 ml MEM containing 5% delipidated fetal bovine serum (FBS) and 5 μM mevinolin. FBS was delipidated using 3% (w/v) Cabosil (Fluka; Ronkonkoma, N.Y.) as described by Weinstein (*Circulation* 59/60 (suppl. II): 54 (1979), which is incorporated herein by reference). Various treatment groups were as follows: peak 3 or peak 4 (concentrated 3× their original concentrations, in ethanol) or 25-hydroxycholesterol (1 μg/ml 25-hydroxycholesterol and 10 μml cholesterol, in ethanol). Cells were incubated an additional 18 hr, then harvested and assayed for luciferase activity using a Bio Orbit 1251 LKB luminometer (Pharmacia/LKB; Piscataway, N.J.).

Figure 3:
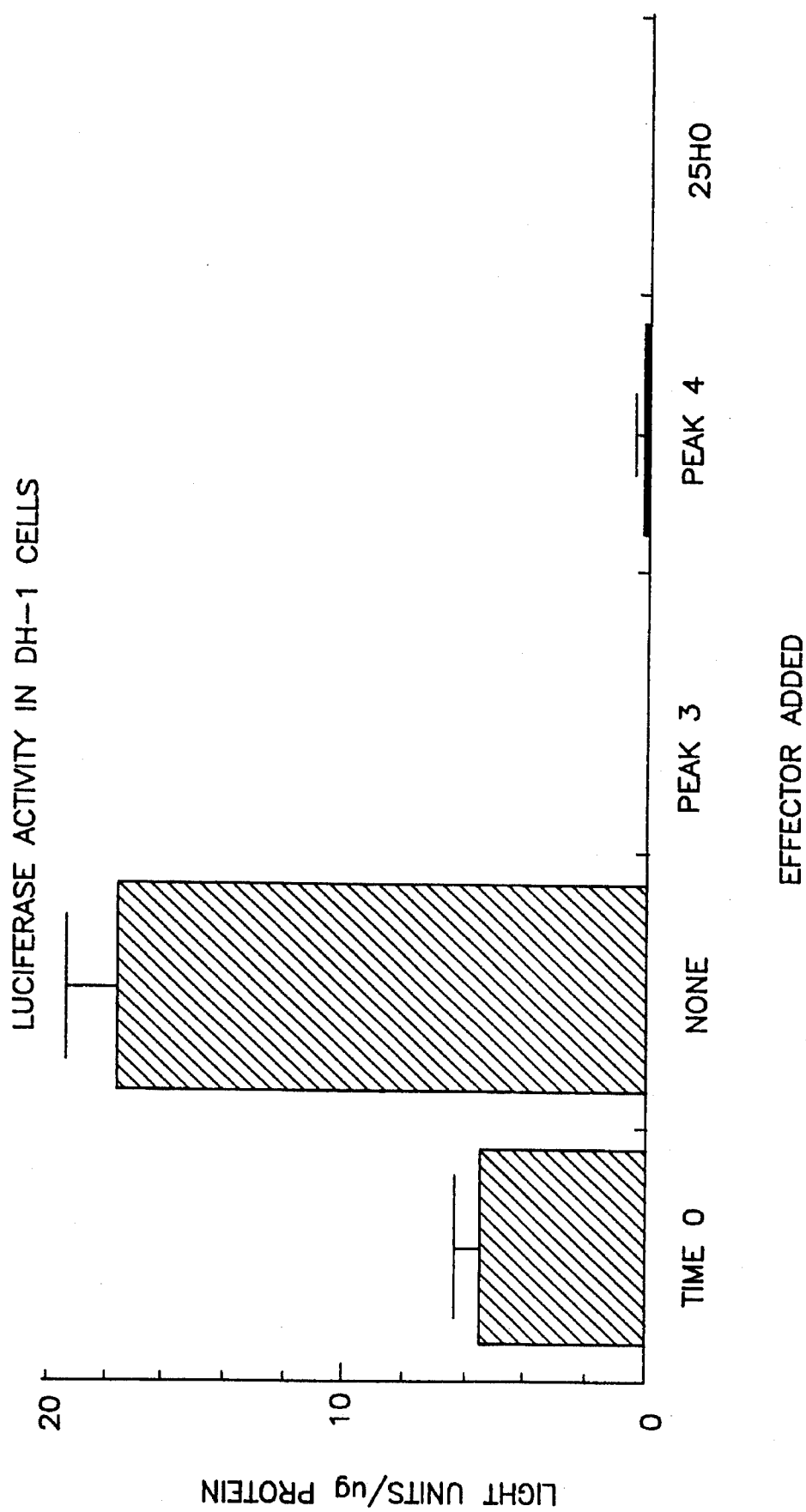
FIG. 3 demonstrates the effect of the cellular factors of the invention to repress transcription from the HMG-CoA reductase promotor. CHO-K1 cells were transfected with a plasmid containing a nucleic acid sequence encoding luciferase under the control of the HMG-CoA reductase promotor (DH1 cells). Luciferase activity was determined in DH1 cells incubated under the following conditions: medium containing 5% serum ("Time 0") or medium containing 5% delipidated medium plus 5 µM mevinolin, alone ("None"), or containing the cellular factors in HPLC peak 3 ("Peak 3"), the cellular factors in HPLC peak 4 ("Peak 4") or 1 µg/ml 25-hydroxycholesterol and 10 µg/ml cholesterol ("25HO"). HPLC peaks 3 and 4 (see FIG. 1) were concentrated in ethanol to ⅓ the original volume of medium collected.

Peak 3, peak 4 and 25-hydroxycholesterol repressed luciferase activity to essentially undetectable levels in the DH1 cells (FIG. 3). These results demonstrate that the cellular factors present in peaks 3 and 4 can repress transcription from the HMG-CoA reductase gene promotor, which results in decreased HMG-CoA reductase activity in a non-hepatic cells. Also, since the cellular factors present in the HPLC fractions can repress the expression of HMG-CoA reductase in wild-type CHO-K1 cells and can induce the expression of 7α-hydroxylase in L35 hepatoma cells (see below), the cellular factors can enter different cell types and are transported to the appropriate intracellular site for effecting their action.

Based on comparison to the activity of other sterols, peak 3 and peak 4 each contain a minimum of about 1 ng cellular factor/60 mm dish of cells. The reduction in luciferase activity was similar to the reduction that occurred when 25-hydroxycholesterol (1 μg/ml) and cholesterol (10 μg/ml) in ethanol were added to the cells. Therefore, if the assumption is made that the UV-absorption at 210 nm of these cellular factors is due to oxysterols and that the absorption by these factors is equivalent to the absorption of 25-hydroxycholesterol, the cellular factors of the invention are approximately 500× more potent than 25-hydroxycholesterol in repressing transcription of the HMG-CoA reductase gene.

B. Up-regulation of 7α-hydroxylase Gene Expression

L35 cells were used to identify the presence of cellular factors that can induce the expression of mRNA encoding 7α-hydroxylase. L35 cells were cultured as described by Leighton et al., supra, 1991.

To assay for cellular factor activity, the culture medium was removed and serum-free medium containing physiologic concentrations of the various HPLC fractions in ethanol were added to L35 cells. Physiologic concentrations were estimated based on the amount of factor present in the medium used for the initial isolation and assuming that 100% of the cellular factor was isolated from the medium. The cells were incubated for 24 hr, then the cells were collected and 7α-hydroxylase mRNA was determined using well known methods (see, for example, Sambrook et al., *Molecular Cloning: A laboratory manual* (Cold Spring Harbor Laboratory Press 1989), which is incorporated herein by reference).

Briefly, RNA was isolated from L35 cells using guanidinium isothiocyanate extraction and poly-$A^+$ mRNA was obtained by affinity chromatography using oligo (dT) cellulose. Poly-$A^+$ mRNA was separated by electrophoresis in a 0.8% agarose gel containing 3% formaldehyde, then transferred to Zetaprobe nylon filters (BioRad; Hercules, Calif.). One μg rat 7α-hydroxylase cDNA (Jelinek et al., supra, 1990) was radiolabelled by nick translation using $\alpha$-$^{35}$P-dCTP (3000 Ci/mmole; Dupont-NEN). The specific activity of the probe was $4 \times 10^8$ cpm/μg. The filters were placed in hybridization solution (0.12M sodium phosphate, pH 7.2/0.25M NaCl/7% SDS/15% formamide) and 100 ng labelled probe was added. Hybridization was allowed to proceed for 18 hr at 44° C., then the filters were washed $2 \times 20$ min in $0.1 \times$ SSC/0.1% SDS at 44° C. (Sambrook et al., supra, 1989). Following washing, 7α-hydroxylase mRNA was visualized by exposing Kodak X-AR5 film at −70° C. for 1–3 days with a Dupont Reflection™ intensifying screen.

Incubation of L35 cells with the cellular factors present in peak 2, peak 3 and peak 4 (FIG. 4; 1, 2 and 3, respectively) resulted in an increase in the relative abundance of 7α-hydroxylase mRNA. The induced mRNA corresponds in size and pattern to 7α-hydroxylase mRNA induced by dexamethasone (not shown). In contrast to the cellular factors in peaks 2 and 3, 25-hydroxycholesterol did not increase 7α-hydroxylase mRNA levels in L35 cells. These results demonstrate that the novel cellular factors, which can repress transcription of the HMG-CoA reductase gene in non-hepatic, also can induce expression of the 7α-hydroxylase gene in L35 cells, which have a phenotype characteristic of adult rat liver.

Although the invention has been described with reference to the examples above, it should be understood that various modifications can be made without departing from the spirit of the invention. Accordingly, the invention is limited only by the following claims.

I claim:

1. A substantially purified cellular factor that regulates the expression of a gene encoding a protein involved in cholesterol homeostasis, wherein said factor elutes at 11.27 minutes by reverse phase-high performance liquid chromatography (RP-HPLC) using acetonitrile:methanol (70:30) as a solvent.

2. The cellular factor of claim 1, wherein said regulation is up-regulation of the 7α-hydroxylase gene.

3. The cellular factor of claim 1, wherein said regulation is down-regulation of the β-hydroxy-β-methylglutaryl coenzyme A (HMG-CoA) reductase gene.

4. A substantially purified cellular factor that regulates the expression of a gene encoding a protein involved in cholesterol homeostasis, wherein said factor elutes at 13.46 minutes by reverse phase-high performance liquid chromatography (RP-HPLC) using acetonitrile:methanol (70:30) as a solvent.

5. The cellular factor of claim 4, wherein said regulation is up-regulation of the 7α-hydroxylase gene.

6. The cellular factor of claim 4, wherein said regulation is down-regulation of the β-hydroxy-β-methylglutaryl coenzyme A (HMG-CoA) reductase gene.

7. A substantially purified cellular factor that regulates the expression of a gene encoding a protein involved in cholesterol homeostasis, wherein said factor elutes at 19.45 minutes by reverse phase-high performance liquid chromatography (RP-HPLC) using acetonitrile:methanol (70:30) as a solvent.

8. The cellular factor of claim 7, wherein said regulation is up-regulation of the 7α-hydroxylase gene.

9. The cellular factor of claim 7, wherein said regulation is down-regulation of the β-hydroxy-β-methylglutaryl coenzyme A (HMG-CoA) reductase gene.

10. A method of reducing the plasma cholesterol level in a mammalian subject having hypercholesterolemia, comprising administering a cellular factor that can regulate the expression of a gene encoding a protein involved in cholesterol homeostasis to the subject, wherein said administration reduces the plasma cholesterol level in said subject.

11. The method of claim 10, wherein said cellular factor is a substantially purified cellular factor that regulates the expression of a gene encoding a protein involved in cholesterol homeostasis, wherein said factor elutes at 11.27 minutes by reverse phase-high performance liquid chromatography (RP-HPLC) using acetonitrile:methanol (70:30) as a solvent.

12. The method of claim 10, wherein said cellular factor is a substantially purified cellular factor that regulates the expression of a gene encoding a protein involved in cholesterol homeostasis, wherein said factor elutes at 13.46 minutes by reverse phase-high performance liquid chromatography (RP-HPLC) using acetonitrile:methanol (70:30) as a solvent.

13. The method of claim 10, wherein said cellular factor is a substantially purified cellular factor that regulates the expression of a gene encoding a protein involved in cholesterol homeostasis, wherein said factor elutes at 19.45 minutes by reverse phase-high performance liquid chromatography (RP-HPLC) using acetonitrile:methanol (70:30) as a solvent.

14. A method of reducing the level of an oxysterol in a mammalian subject, comprising administering to the subject a cellular factor that can induce 7α-hydroxylase, which metabolizes the oxysterol, thereby reducing the level of said oxysterol in said subject.

15. The method of claim 14, wherein said cellular factor is a substantially purified cellular factor that regulates the expression of a gene encoding a protein involved in cholesterol homeostasis, wherein said factor elutes at 11.27 minutes by reverse phase-high performance liquid chromatography (RP-HPLC) using acetonitrile:methanol (70:30) as a solvent.

16. The method of claim 14, wherein said cellular factor is a substantially purified cellular factor that regulates the expression of a gene encoding a protein involved in cholesterol homeostasis, wherein said factor elutes at 13.46 minutes by reverse phase-high performance liquid chromatography (RP-HPLC) using acetonitrile:methanol (70:30) as a solvent.

17. The method of claim 14, wherein said cellular factor is a substantially purified cellular factor that regulates the expression of a gene encoding a protein involved in cholesterol homeostasis, wherein said factor elutes at 19.45 minutes by reverse phase-high performance liquid chromatography (RP-HPLC) using acetonitrile:methanol (70:30) as a solvent.

* * * * *

UNITED STATES PATENT AND TRADEMARK OFFICE
CERTIFICATE OF CORRECTION

PATENT NO. : 5,622,779
DATED : Apr. 22, 1997
INVENTOR(S) : Roger Davis

It is certified that error appears in the above-identified patent and that said Letters Patent is hereby corrected as shown below:

In column 9, line 63, please delete "in these" and replace therefor with --in three--.

Signed and Sealed this

Fourteenth Day of December, 1999

*Attest:*

Q. TODD DICKINSON

*Attesting Officer*     *Acting Commissioner of Patents and Trademarks*